US00PP18617P2

(12) United States Plant Patent
Blom

(10) Patent No.: US PP18,617 P2
(45) Date of Patent: Mar. 18, 2008

(54) ***ECHINACEA* PLANT NAMED 'COCONUT LIME'**

(50) Latin Name: *Echinacea purpurea*
Varietal Denomination: Coconut Lime

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 11/527,834

(22) Filed: Sep. 27, 2006

(51) Int. Cl.
*A01H 5/00* (2006.01)

(52) U.S. Cl. ..... Plt./263
(58) Field of Classification Search ..... Plt./258, Plt./263
See application file for complete search history.

(56) References Cited

PUBLICATIONS

UPOV ROM GTITM Computer Database, GTI Jouve Retrieval Software 2007/02 Citations for 'Coconut Lime'.*

* cited by examiner

*Primary Examiner*—Wendy Haas
(74) *Attorney, Agent, or Firm*—C. A. Whealy

(57) ABSTRACT

A new and distinct cultivar of *Echinacea* plant named 'Coconut Lime', characterized by its upright and columnar plant habit; moderately vigorous growth habit; freely basal branching habit; and large inflorescences with white and yellow green-colored ray florets and yellow green-colored disc florets.

2 Drawing Sheets

Botanical designation: *Echinacea purpurea.*
Cultivar denomination: 'Coconut Lime'.

BACKGROUND OF THE INVENTION

The present invention relates to a new and distinct cultivar of *Echinacea* plant, botanically known as *Echinacea purpurea,* and hereinafter referred to by the name 'Coconut Lime'.

The new *Echinacea* originated from an open-pollination in IJsselstein, The Netherlands in July, 2004, of an unnamed selection of *Echinacea purpurea,* not patented, as the female, or seed, parent with an unknown selection of *Echinacea purpurea,* as the male, or pollen, parent. The new *Echinacea* was discovered and selected by the Inventor as a single flowering plant from within the progeny of the stated open-pollination grown in a controlled environment in Zuidwolde, The Netherlands.

Asexual reproduction of the new *Echinacea* by micropropagation a controlled environment in The Netherlands since 2005, has shown that the unique features of this new *Echinacea* are stable and reproduced true to type in successive generations.

SUMMARY OF THE INVENTION

The cultivar Coconut Lime has not been observed under all possible environmental conditions. The phenotype may vary somewhat with variations in environment such as temperature and light intensity, without, however, any variance in genotype.

The following traits have been repeatedly observed and are determined to be the unique characteristics of 'Coconut Lime'. These characteristics in combination distinguish 'Coconut Lime' as a new and distinct cultivar of *Echinacea:*

1. Upright and columnar plant habit.
2. Moderately vigorous growth habit.

3. Freely basal branching habit.
4. Large inflorescences with white and yellow green-colored ray florets and yellow green-colored disc florets.

Plants of the new *Echinacea* differ primarily from plants of the female parent selection in ray and disc coloration.

Plants of the new *Echinacea* can be compared to plants of the cultivar Pink Shuttles, disclosed in U.S. Plant patent application Ser. No. 11/527,811. In side-by-side comparisons conducted in Vleuten, The Netherlands, plants of the new *Echinacea* differed from plants of the cultivar Pink Shuttles in the following characteristics:

1. Plants of the new *Echinacea* were more freely branching than plants of the cultivar Pink Shuttles.
2. Plants of the new *Echinacea* and the cultivar Pink Shuttles differed in inflorescence coloration.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical flowering plant of 'Coconut Lime' grown in a container.

The photograph at the top of the second sheet is a close-up view of a typical inflorescence of 'Coconut Lime'.

The photograph at the bottom of the second sheet is a close-up view of a typical leaf of 'Coconut Lime'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Vleuten, The Netherlands during the summer in an outdoor nursery and under conditions and practices which approximate those generally used in commercial *Echinacea* production. During the production of the plants, day temperatures ranged from −5° C. to 35° C. and night temperatures ranged from −8° C. to 20° C. Measurements and numerical values represent averages for typical flowering plants. Plants were about 16 months year old when the photographs and description were taken.

Botanical classification: *Echinacea purpurea* cultivar Coconut Lime.

Parentage:

*Female parent.*—Unnamed selection of *Echinacea purpurea,* not patented.

*Male parent.*—Unknown selection of *Echinacea purpurea,* not patented.

Propagation:

*Type.*—by micropropagation.

*Time to initiate roots.*—About one week at 25° C.

*Time to produce a rooted young plant.*—About five weeks at 21° C.

*Root description.*—Fine, fibrous; pale cream white in color.

*Rooting habit.*—Freely branching; moderately dense.

Plant description:

*Plant form/growth habit.*—Upright and columnar plant habit; freely basal branching with about nine primary branches developing per plant. Moderately vigorous growth habit.

*Plant height.*—About 73 cm.

*Plant diameter or spread.*—About 32 cm.

*Basal branches.*—Length: About 55.6 cm. Diameter: About 4 mm. Internode length: About 9.8 cm. Aspect: Mostly upright. Strength: Strong. Texture: Pubescent; rough. Color: 144A.

Foliage description:

*Arrangement.*—Alternate, simple.

*Length.*—About 9 cm.

*Width.*—About 3.6 cm.

*Shape.*—Narrowly ovate to ovate.

*Apex.*—Acute.

*Base.*—Attenuate.

*Margin.*—Irregularly and sparsely serrate.

*Texture, upper and lower surfaces.*—Pubescent; rough.

*Venation pattern.*—Pinnate.

*Color.*—Developing foliage, upper surface: 137A to 137B. Developing foliage, lower surface: 137C. Fully expanded foliage, upper surface: 137A; venation, 144B. Fully expanded foliage, lower surface: 137C; venation, 144B to 144C.

*Petiole length.*—About 8.5 cm.

*Petiole diameter.*—About 1 mm.

*Petiole texture, upper surface.*—Smooth, glabrous.

*Petiole texture, lower surface.*—Sparsely pubescent.

*Petiole color, upper and lower surfaces.*—144A.

Inflorescence description:

*Appearance.*—Rotate single inflorescence form with ray and disc florets. Inflorescences positioned above the foliage on strong peduncles and face upright. About two inflorescences develop per lateral branch. Inflorescences not persistent.

*Fragrance.*—Faint; sweet.

*Time to flower.*—Plants flower continuously from late July to late September in The Netherlands.

*Inflorescence longevity.*—Inflorescences maintain good substance for about three weeks on the plant.

*Inflorescence bud.*—Height: About 1.1 cm. Diameter: About 2.2 cm. Shape: Flattened globular. Color: Between 143A and 146A.

*Inflorescence size.*—Diameter: About 7.5 cm. Depth (height): About 2 cm. Disc diameter: About 2.5 cm. Receptacle height: About 9 mm. Receptacle diameter: About 1.6 cm.

*Ray florets.*—Length: About 3.8 cm. Width: About 1 cm. Shape: Oblanceolate. Apex: Praemorse. Base: Cuneate. Margin: Entire. Texture, upper and lower surfaces: Smooth, glabrous. Number of ray florets per inflorescence: About 13 arranged in a single whorl. Aspect: Drooping. Color: When opening, upper surface: 150D to 155C; towards the apex, 145C to 145D. When opening, lower surface: 150C; towards the apex, 145C to 150B to 150C. Fully opened, upper surface: 155C; towards the apex, 145C to 145D. With development, 145B; towards the apex, 145A. Fully opened, lower surface: 150C; towards the apex, 145C to 150B to 150C. With development, 145A.

*Disc florets.*—Length: About 1.4 cm. Diameter: About 3.5 mm. Shape: Tubular, enlarged; apices acute. Number of disc florets per inflorescence: About 450. Texture, upper and lower surfaces: Smooth, glabrous. Color: Immature, inner and outer surfaces: 150B; towards the base, 144A to 144B. Mature, inner surface: 155C to 150D; towards the base, 144A to 144B. Mature, outer surface: 145B to 145C; towards the base, 144A to 144B.

*Receptacle spines.*—Quantity: One per disc floret. Shape: Acicular. Apex: Acute. Base: Attenuate. Texture: Smooth, glabrous. Color: Apex: 25B. Midsection: 143A. Base: 144C to 144D.

*Involucral bracts.*—Quantity per inflorescence: About 46 in about three whorls. Length: About 1 cm. Width: About 1.5 mm. Shape: Lanceolate. Apex: Acute. Base: Cuneate. Margin: Entire. Texture, upper surface: Smooth, glabrous. Texture, lower surface: Densely pubescent. Color, upper and lower surfaces: 137A.

*Peduncles.*—Length: About 10 cm. Diameter: About 3.5 mm. Strength: Strong. Aspect: Mostly upright. Texture: Pubescent; rough. Color: 144C.

*Reproductive organs.*—Androecium: Not observed. Gynoecium: Only observed in disc florets. Pistil length: About 5.5 mm. Stigma shape: Cleft; reflexed. Stigma color: 151B. Style length: About 4.5 mm. Style color: 145C. Ovary color: 157D. Fruits/seeds Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind, have been observed to be hardy to USDA Zone 4 and to tolerate high temperatures of about 35° C.

It is claimed:

1. A new and distinct *Echinacea* plant named 'Coconut Lime' as illustrated and described.

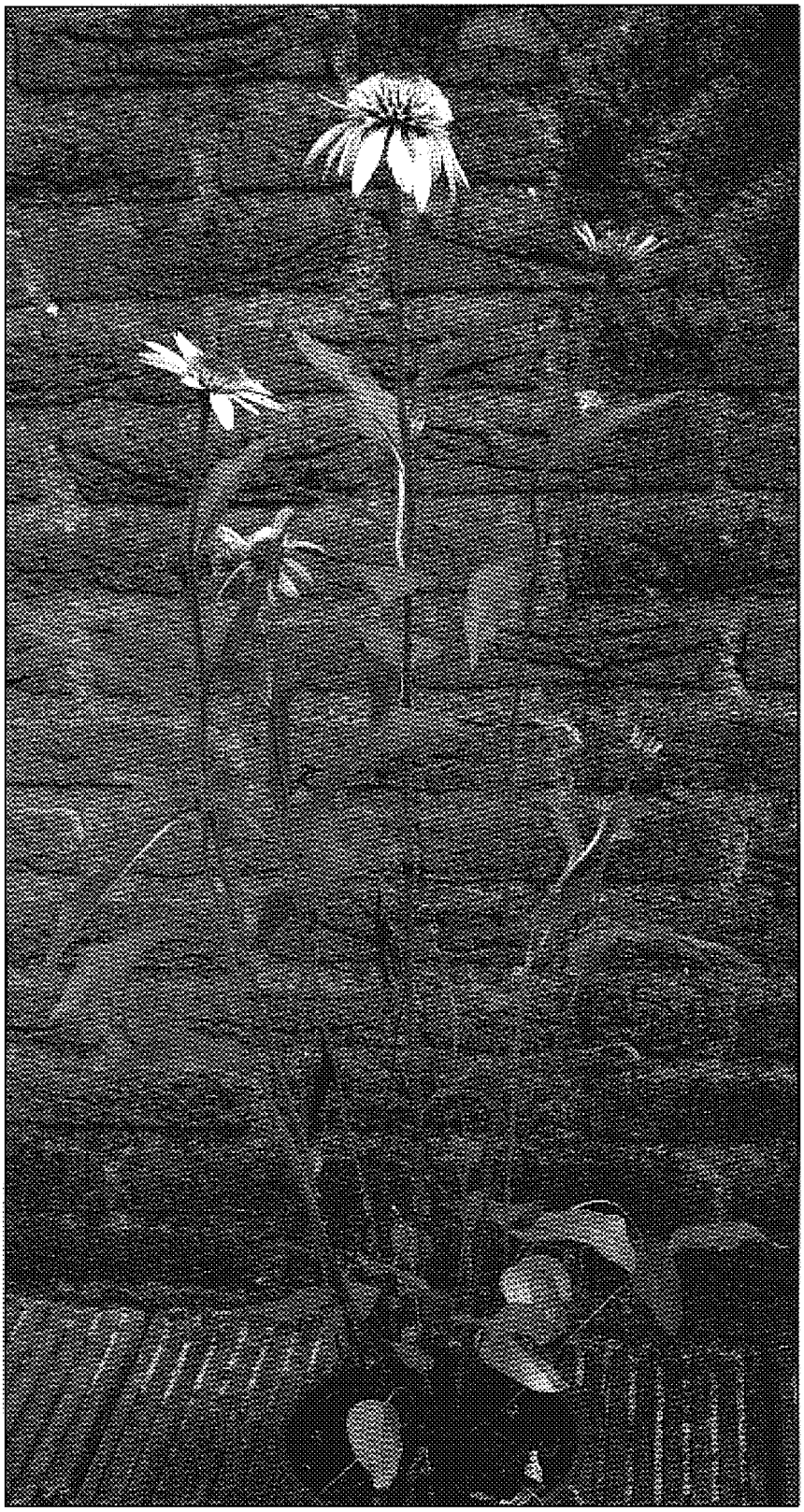

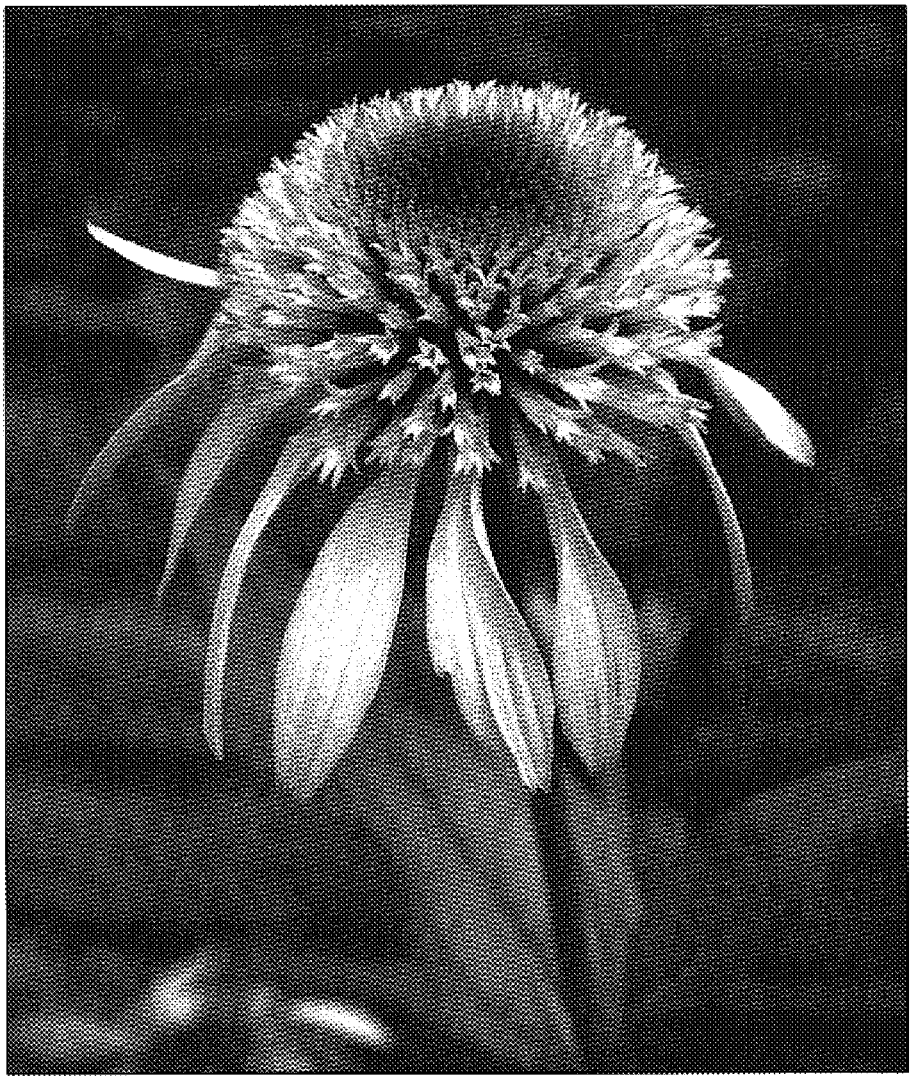
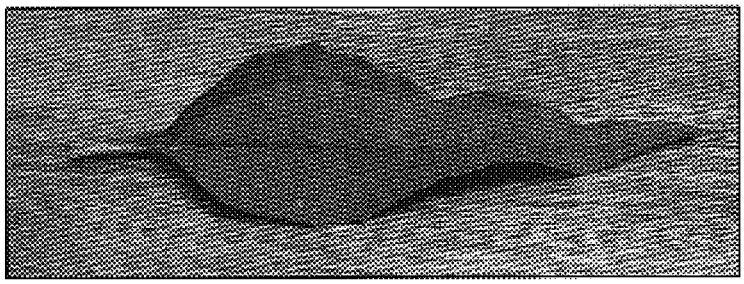

* * * * *